United States Patent [19]

Klauser

[11] 4,057,732

[45] Nov. 8, 1977

[54] FILM HOLDER FOR BITE-WING RADIOGRAPHS

[76] Inventor: Rolf Marcus Klauser, Luzernerstrasse 6, 6010 Kriens, Switzerland

[21] Appl. No.: 655,434

[22] Filed: Feb. 4, 1976

[51] Int. Cl.² .................................................. G03B 41/16
[52] U.S. Cl. .................................................. 250/479
[58] Field of Search .................. 250/479, 478, 475

[56] References Cited

U.S. PATENT DOCUMENTS

| 2,034,049 | 3/1936 | Levy | 250/479 |
| 2,392,109 | 1/1946 | Vlock | 250/479 |
| 2,553,028 | 5/1951 | Wright | 250/479 |
| 2,777,068 | 1/1957 | Bowser | 250/479 |
| 3,003,062 | 10/1961 | Updegrave | 250/479 |

*Primary Examiner*—Craig E. Church
*Attorney, Agent, or Firm*—Imirie, Smiley & Guay

[57] ABSTRACT

The present invention relates to a film holder for bite-wing X-ray films with a centering device for the X-ray cone comprising an indicator rod portion extending parallel to a central guide axis of the holder and provided for guiding the X-ray cone and an index projection indicating the horizontal medial axis of the X-ray film and its end indicating the central axis.

The film holder is preferably made of plastics material to be used once, providing maximum hygiene, whereas the indicator rod is provided with fracture means, the holder thus being adaptable for all types of X-ray cones.

3 Claims, 2 Drawing Figures

FILM HOLDER FOR BITE-WING RADIOGRAPHS

BACKGROUND OF THE INVENTION

The present invention relates to a film holder for bite-wing radiographs and having an X-ray cone centering device.

In order to provide an as true as possible print of teeth, i.e. one which is undistorted, it is necessary to position properly an X-ray film located in a holding device and to bring the X-ray cone up to the X-ray film. A film holder having a centering device is known from the U.S. Pat. No. 3,003,062 and is provided to enable all the teeth to be X-rayed. For this purpose the holder is provided with a rotatable shank, in order to be usable on either the right-hand or left-hand side of the mouth, and for either the lower or upper teeth respectively to be exposed. This film holder is intended for a specific type of X-ray cone and, moreover, is intended to be used such that after each exposure only the film is changed and the holder is then re-used. This re-use, however, provides a problem with respect to hygiene since it is difficult for the holder to be sterilized and also such holder may be used only with a certain type of cone. The instruments of the Rinn Corporation, Elgin, Ill., U.S.A., concerned with this U.S. Patent are modified in essential points and have a clamping clip for an X-ray film, a mouthpiece, a metal rod bent at right angles and a ring guided thereon for centering the X-ray cone. Compared with the ebodiments of U.S. Pat. No. 3,003,062, the rotatable shank has been omitted and replaced by a ring functioning as the centering system. Besides the problems relating to hygiene, which result from the repeated application of the instrument, the latter holder has the disadvantage in that it is applicable only to a definite type of X-ray cone.

Also to secure the X-ray film, known discardable film holders made of cardboard or plastic material are used and are either slipped over the X-ray film or resiliently retain such. These X-ray film holders, however, have no device whatsoever to guide and center the X-ray cone so that the dentist is substantially dependent on visual judgement since the cone has applied thereto only a graduation to determine the inclination relative to the floor and such exposures are only possible with patients in the sitting position.

SUMMARY OF THE INVENTION

It is an object of the present invention to provide a film holder for bite-wing radiographs which is very simple and cheap to manufacture and which presents a reliably good guidance and centering to most existing X-ray cones which may be used for patients who are reclining or sitting, and which holders can also be used in an extremely hygienic manner.

According to the present invention there is provided a film holder for use in taking bite-wing X-ray exposures comprising a resilient clip device at one end of the film holder for receiving an X-ray film of optional size and a centering device comprising an indicator rod portion extending parallel to a central guide axis of the holder and provided for guiding an X-ray cone and an index projection extending at right angles to said indicator rod; said index projection indicating the horizontal medial axis of the X-ray film and its end indicating the central axis.

The film holder according to the invention is preferably used only once and, by virtue of its simple construction, such use is not prohibitive from a cost point of view.

The invention will now be described further, by way of example, with reference to the accompanying drawings.

DESCRIPTION OF THE PREFERRED EMBODIMENTS

Figure 1:
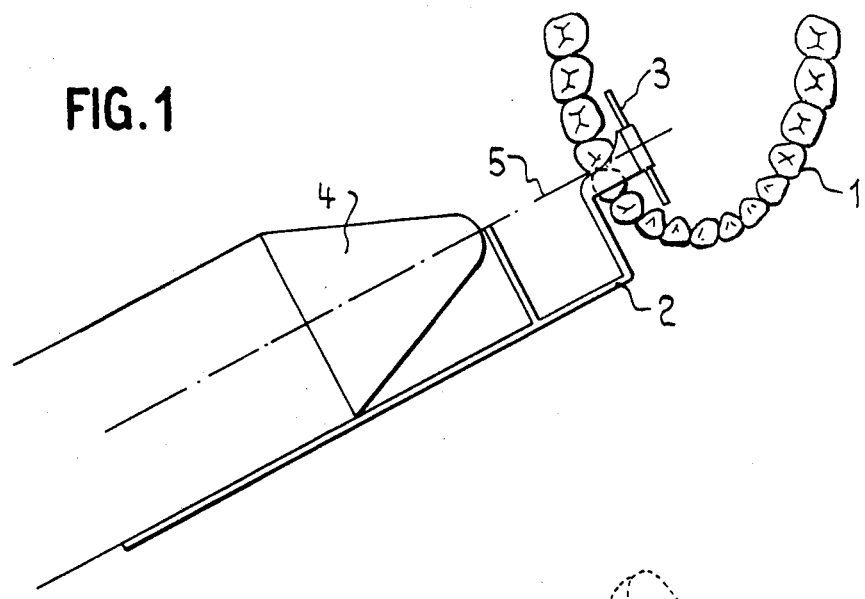
FIG. 1 is a schematic illustration of the relative positioning of a film holder, teeth and an X-ray cone.
Figure 2:
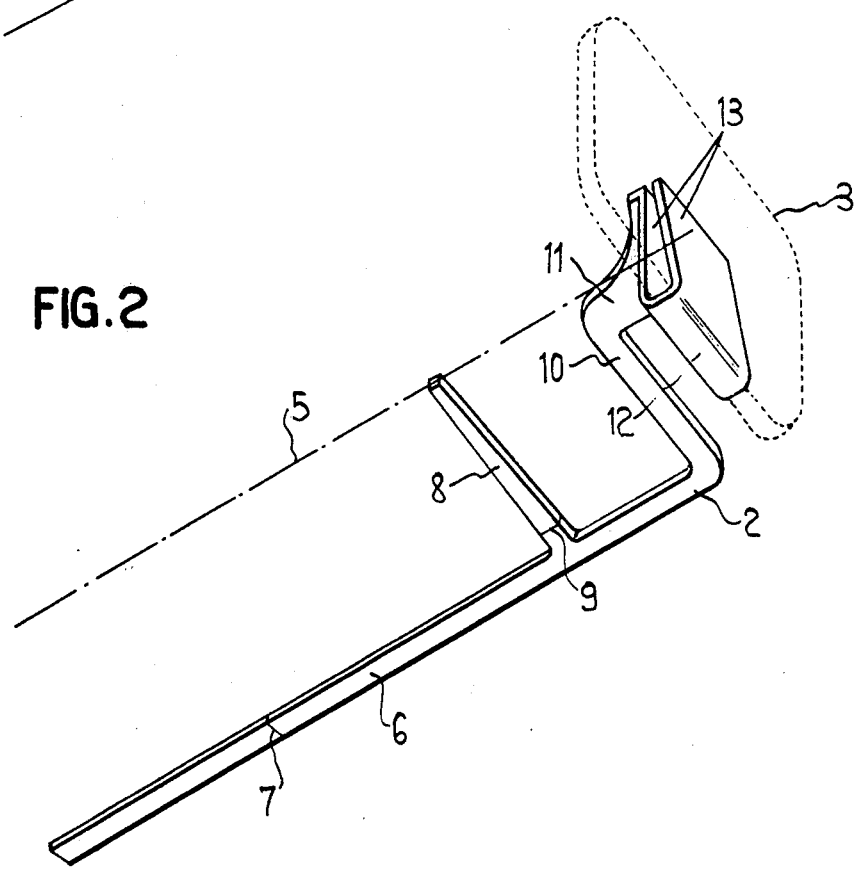
FIG. 2 is a perspective view of the film holder according to the present invention.

In FIG. 1 there is shown a row of teeth 1, a film holder 2, an intra-orally located X-ray film 3 and an X-ray cone 4 having a central axis 5. FIG. 2 shows an indicator rod 6 which serves to guide the X-ray cone and is located parallel to the main axis of said cone so that this main axis as shown through the momentarily used X-ray cone extends through the center of the X-ray film. In the present illustration the indicator rod is intended for a long-cone, but when using a short cone, the indicator rod is readily broken off at a fracture point 7.

On the film holder 2 the end of the index 8 indicates the main axis and said index is arranged at right angles to the indicator rod. Moreover, the index determines the horizontal central line of the X-ray film. The index 8 has a marking 9 which facilitates the alignment of X-ray cones — the external diameter of said cone being smaller than twice the length of the index 8. At a certain distance from the index, the indicator rod 6 merges into an angle portion 10 extending parallel to the index 8 and at right angles to rod 6 — thus in the extension of the main axis; a bit or bite portion 11 extending from the end of portion 10 and being formed as a thin, ribbed plate. The bite portion 11 should be as thin as possible to permit the patient to bite firmly thereon and to enable the film holder to be rigidly retained in a definite position. The bite portion 11 runs into a resilient clamp or clip device 12 which is U-shaped and which serves for the firm and secure holding of the X-ray film 3. The clip 12 has two shanks 13 of a length such that the medial line of the widest obtainable X-ray film on the market coincides with the index 8 when the film is completely inserted in the clip. X-ray films of smaller dimensions do not require to be completely inserted in the clip since centering by sight suffices for these exposures.

The film holder is preferably made of plastic material which should be inherently stable so that when the patient bites firmly, the bite portion 11 is not deformed or only minimally deformed. Moreover, the plastic material should also be resilient since the clip has to be resilient so as to retain reliably the X-ray film. Furthermore, a plastic material has to be chosen which permits X-rays to pass unhindered therethrough since the X-rays have to penetrate the index, the angle member and the clip. The plastic material must, of course, also be of such nature as to remain clean and hygienic.

From the above description it will be appreciated that the film holder is suitable for all kinds of X-ray cones, i.e. short and long cones, for cylindrical, conical or tapered cones, for pointed and flat cones which, of course, must not exceed a certain external diameter — the maximum diameter usable being given by twice the length of the index respectively.

It is consequently possible to apply several markings on the index 8 — the dentist first having to measure his cone and may use the suitable marking, should the cone diameter be smaller. It is just as much possible to provide several fracture points on the indicator rod.

The film holder is suitable for any X-ray technique, thus both for right angle (extension-cone-paralleling technique) and bisected angle X-ray technique whereby, in the case of right angle X-ray technique, the film holder may also be used when the patient is in a reclined position.

The use of the film holder is extremely simple. The X-ray film to be used is slid into the clip and aligned on the index. Subsequently the film, as indicated in FIG. 1, is placed against the inside surfaces of the lower or upper teeth, whereupon the patient has to bite on the bite whereby the film is automatically aligned with regard to the teeth. Subsequently the X-ray tube is aligned on the indicator rod 6 and by means of the index 8, whereby the indicator rod, if necessary, may be shortened at the fracture point 7, so that it is possible in any case to slide the X-ray cone right against the index resting on the cheek. After exposure the X-ray film is removed and the film holder will normally be discarded. This single use of the X-ray film holder avoids the hitherto unhygienic repeated use of devices which could not be readily cleaned.

What is claimed is:

1. A film holder for bite-wing radiographs comprising an elongate centering device having at one end a resilient clip device with a bite portion therebetween to enable the bite portion to be clamped between a patients teeth with the clip device within the patients mouth and the centering device extending outwardly from the patients face, said clip device having two shanks for receiving an X-ray film of optional size and of a length corresponding to the distance from the edge to the medial line of the widest X-ray film to be used; said centering device comprising an indicator rod portion extending parallel to a central guide axis of the holder and provided for guiding an X-ray cone relative to an X-ray film in said clip device; and an index projection extending at right angles to said indicator rod and secured thereto intermediate its ends; and index projection indicating the horizontal medial axis of the X-ray film and its end indicating the position of the central axis; said holder being integrally formed of plastic material.

2. A film holder as claimed in claim 1, in which the indicator rod is provided with at least one fracture means or line to permit shortening of the rod.

3. A film holder as claimed in claim 1, in which the index has at least one marking thereon for facilitating alignment of X-ray cones of different radiuses.

* * * * *

UNITED STATES PATENT AND TRADEMARK OFFICE
CERTIFICATE OF CORRECTION

PATENT NO. : 4,057,732
DATED : November 8, 1977
INVENTOR(S) : ROLF MARCUS KLAUSER It is certified that error appears in the above-identified patent and that said Letters Patent are hereby corrected as shown below:

Claim 1, line 16 (Column 4, line 17), change "and" to -- said --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks